(12) United States Patent
Mioskowski et al.

(10) Patent No.: US 7,420,087 B2
(45) Date of Patent: Sep. 2, 2008

(54) METHOD FOR PREPARING 4-HYDROXYISOLEUCINE DIASTEREOISOMERS AND ENANTIOMERS AND DERIVATIVES THEREOF

(75) Inventors: Charles Mioskowski, Strasbourg (FR); Alain Wagner, Strasbourg (FR); Sandra De Lamo Marin, Strasbourg (FR); Cedric Catala, Strasbourg (FR); Jean-Michel Becht, Brunstatt (FR)

(73) Assignees: Centre National de la Recherche Scientifique (C.N.R.S.), Paris (FR); Universite Louis Pasteur, Strasbourg (FR)

( * ) Notice: Subject to any disclaimer, the term of this patent is extended or adjusted under 35 U.S.C. 154(b) by 82 days.

(21) Appl. No.: 10/537,293

(22) PCT Filed: Dec. 1, 2003

(86) PCT No.: PCT/FR03/03542

§ 371 (c)(1),
(2), (4) Date: Jan. 24, 2006

(87) PCT Pub. No.: WO2004/052836

PCT Pub. Date: Jun. 24, 2004

(65) Prior Publication Data

US 2006/0205817 A1    Sep. 14, 2006

(30) Foreign Application Priority Data

Dec. 2, 2002   (FR) ................................. 02 15165

(51) Int. Cl.
C07C 229/00   (2006.01)
C07D 305/12   (2006.01)

(52) U.S. Cl. ..................................... 562/567; 549/321

(58) Field of Classification Search ................. 562/567; 549/321

See application file for complete search history.

(56) References Cited

U.S. PATENT DOCUMENTS 5,763,483 A * 6/1998 Bischofberger et al. ...... 514/529
5,900,237 A * 5/1999 Napper et al. ............ 424/175.1

OTHER PUBLICATIONS

International Search Report for PCT/FR03/03542 dated Apr. 15, 2004.
Caplan et al.., *Vinylogous Amide Analogues of Diaminopimelic Acid (DAP) as Inhibitors of Enzymes Involved in Bacterial Lysine Biosynthesis*, Organic Letters, vol. 2, No. 24, 2000, pp. 3857-3860; XP-02247986.
Büchi et al., *Interchange of Functionality in Conjugated Carbonyl Compounds through Isoxazoles*, Journal of the American Chemical Society, vol. 94, No. 26, Dec. 27, 1972; pp. 9128-9132; XP-002247987.

* cited by examiner

*Primary Examiner*—Sikarl A Witherspoon
(74) *Attorney, Agent, or Firm*—Nixon & Vanderhye P.C.

(57) ABSTRACT

The invention concerns a method for preparing 4-hydroxyisoleucine diastereoisomers and enantiomers and derivatives thereof of general formula (I), characterized in that it consists in reducing an isoxazole derivative of formula (II) in conditions directly resulting in the derivatives of formula (I), or in obtaining at least a lactone of structure (III) in racemic form (s), or a enantiomerically enriched mixture, followed by opening, in basic conditions, in an aprotic or protic solvent, the desired lactone(s) and, optionally, separating the desired form. The invention is useful for preparing in particular (2S, 3R, 4S)-4-hydroxyisoleucine.

23 Claims, 2 Drawing Sheets

METHOD FOR PREPARING 4-HYDROXYISOLEUCINE DIASTEREOISOMERS AND ENANTIOMERS AND DERIVATIVES THEREOF

The present application is a 371 U.S. national phase of PCT/FR2003/003542, filed 1 Dec. 2003, which claims benefit of FR02/15165, filed 2 Dec. 2002, the entire contents of each of which is hereby incorporated by reference.

The invention relates to a method of preparing diastereoisomers and enantiomers of 4-hydroxyisoleucine and derivatives thereof, this term covering the analogs obtainable by the method of the invention. It relates in particular to the preparation of (2S,3R,4S)-4-hydroxyisoleucine (4-OH-iLeu for short).

4-OH-iLeu is a natural product, isolated from fenugreek seed, corresponding to the formula A:

This product is active in particular against type II diabetes, but the amounts obtainable by extraction are insufficient to supply the needs of populations affected by this type of diabetes. The advantage of a total synthesis which would allow this shortfall to be remedied is measured accordingly.

A number of methods have been proposed to date, but have nevertheless proved not to be capable of exploitation on the industrial scale.

The inventors have succeeded in overcoming this problem and in developing a method comprising a reduced number of steps, by virtue of the selection of specific reaction products and specific operating conditions.

This method allows the diastereoisomers and enantiomers of 4-hydroxyisoleucine and derivatives thereof to be obtained with high yields. In particular, 4-OH-iLeu is obtained with yields which may exceed 40%. Advantageously this process also allows derivatives of 4-hydroxyisoleucine to be synthesized.

The aim of the invention is accordingly to provide an economic method of synthesizing α-amino acids of general formula I in which $R_1$ and $R_2$ represent
  a hydrogen atom or
  one of $R_1$ or $R_2$ represents a hydrogen atom and the other substituent is a radical $R_a$, an acyl group —$COR_a$, in particular acetyl, or else a functional group —$COOR_a$, —$SO_2R_a$ or —$N(R_a,R_b)$, $R_a$ and $R_b$, which are identical or different, being an optionally substituted linear or branched C1-C12 alkyl radical, an optionally substituted aryl group containing one or more aromatic rings, comprising 5 to 8 C, or aralkyl, the alkyl substituent and the aryl group being as defined above, or
  $R_1$ and $R_2$ both represent a substituent as defined above, characterized in that it comprises reducing an isoxazole derivative of formula II in which
  $R_a$ is as defined above, and
  $R_3$ represents a hydrogen atom or $R_a$, and
  $R_4$ exhibits the significations of $R_a$, with the exception of a hydrogen atom, under conditions leading directly to derivatives of formula I or to at least one lactone of structure III in racemic form(s), or an enantiomerically enriched mixture, followed by the opening, under basic conditions, in a protic or aprotic solvent, of the desired lactone or lactones and, if necessary, the separation of the required form.

A process of choice for the opening of the lactone ring comprises the use of LiOH in THF.

According to one preferred embodiment of the invention said lactone of structure III is obtained by reducing said isoxazole derivative of formula II, leading to a mixture containing 4 lactones L-1, L-2, L-3 and L-4:

L-4

It will be noted that, where $R_3$ represents a hydrogen atom in the isoxazole of formula II, a group $R_a$ is introduced subsequently into the intermediates obtained.

According to one variant embodiment the desired lactone or lactones is or are separated in racemic or in enantiomerically pure form.

According to the catalysts and conditions that are used it is possible to promote the formation of one of the lactones and/or of one of the enantiomers. Examples are given for illustration in the experimental section.

In accordance with the invention the various lactones in which $R_1$ and/or $R_2$ represent a hydrogen atom may be substituted, in particular alkylated, carbamylated, sulfonylated, acylated, especially acetylated. For this purpose use is made, in particular, of an appropriate alkylating, carbamylating, sulfonylating or acylating agent, advantageously acetic anhydride for synthesizing the acetyl derivatives.

According to a variant preparation of the α-amino acid derivatives of structure I of the invention, an isoxazole of formula II in which $OR_a$ represents a group amenable to hydrogenolysis, such as the benzyl group, is reduced. This reduction step is carried out in a basic medium when $R_a$ is other than a benzyl group.

The intermediates formed during the step of reducing the isoxazole derivative of formula II can be isolated if desired. As indicated above in relation to the lactones, the products in which $R_1$ and/or $R_2$ represent a hydrogen atom may be substituted, in particular alkylated, carbamylated, sulfonylated or acylated, especially acetylated. For this purpose use is made in particular of an appropriate alkylating, carbamylating, sulfonylating or acylating agent, advantageously acetic anhydride for synthesizing the acetyl derivatives. It is important to note that, depending on the catalyst used, it is possible to enrich the product in a given diastereoisomeric and/or enantiomeric form.

Figure 1:
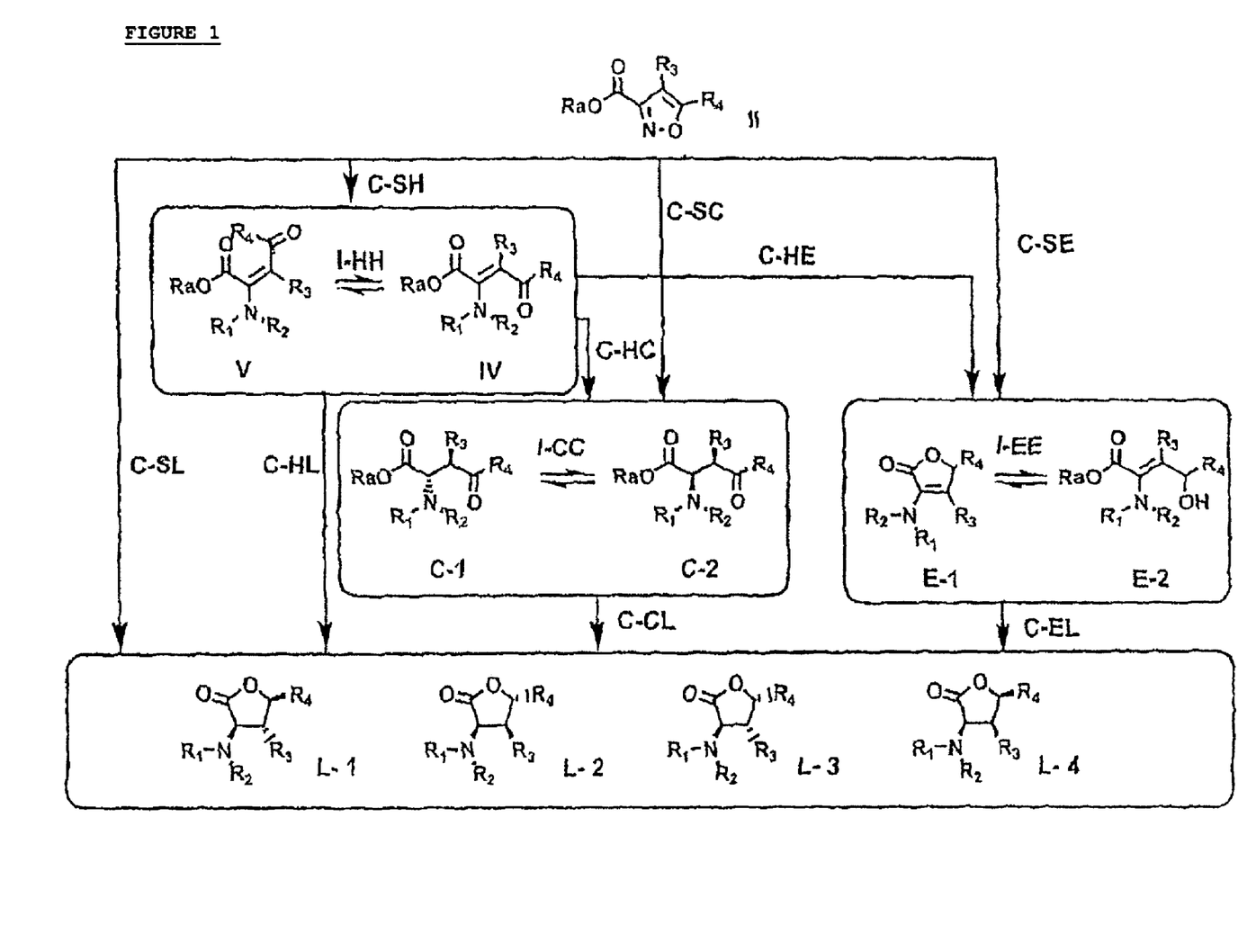
FIG. 1 shows reaction schemes illustrating the procedural variants for obtaining, from the isoxazole derivative of formula III the lactones L-1 to L-4.

According to the operating conditions employed, denoted hereinafter by C-SH, C-SC, C-SE, or C-SH followed by C-HC or by C-HE, these products are different (see FIG. 1).

Thus, according to C-SH. conditions, operation takes place, for example, in an ethanol/water medium, to which a solution of RNi in ethanol and the isoxazole derivative of formula II are added, and the mixture is purged with hydrogen.

The reaction medium is subsequently stirred under a hydrogen pressure of the order of 1 atmosphere at ambient temperature, leading to derivatives IV and V, which can be isolated, for example, by chromatography on silica with a yield of the order of 80%.

IV

V

One variant of the invention allows the compounds of formulae IV and V to be obtained directly from the compound of structure VI:

VI by reaction with the amine of formula $NH(R_1,R_2)$, advantageously in the presence of an acidic catalyst and a dehydrating agent.

The mixture of the 4 lactones L-1, L-2, L-3 and L-4 is recovered and the required lactone is isolated if desired.

One exemplary embodiment of the invention consists in promoting the formation of the lactone L-1 by conducting the reduction in an RNi/DABCO mixture in ethanol, whereas the C1-C2 products are obtained directly if the reaction is conducted in a system such as Pd/C/DABCO in ethanol or Pd/C/triethylamine in ethanol.

As a variant, the compounds C-1 and C-2

C-1

C-2 are obtainable according to C-HC conditions, by subjecting V, at the outcome of the C-SH step, to the action of a reduction catalyst and in a solvent, in the presence of a hydrogen source, for example, Pd/C in ethanol, in the presence of hydrogen. This gives a C-1/C-2 mixture of the order of 70/30 with a yield of approximately 55%

The required mixture of lactones can then be obtained by the C-CL route.

To obtain the lactone L-2 on a majority basis, C-1 in ethanol is subjected advantageously to the action of $NaBH_4$. The lactone may thus be obtained with a yield of the order of 75%, the remainder representing the lactone L-4.

By operating with a mixture of ethanol and water to which a solution of catalyst, for example, of RNi in ethanol and C-1 is added, it is possible to form the lactone L-4 predominantly.

According to advantageous treatment conditions, the reaction mixture is brought to 0° C. and purged with hydrogen, and then subjected to stirring under hydrogen pressure. The mixture of the 4 lactones, L-1, L-2, L-3 and L-4 is obtained quantitatively. The lactone L-4 can be isolated, by HPLC for example, with a yield of approximately 75%, the remainder being formed essentially by the lactone L-2.

The lactone L-3 can be obtained on a majority basis by operating as indicated above but using C-2. The lactone L-3 may then be isolated, by HPLC for example, with a yield of approximately 75%, the remainder being formed essentially by the lactone L-1.

As a variant, the compounds E-1 and E-2 may be obtained according to C-HE conditions.

Thus, the synthesis of E-2 may be carried out starting from IV or V, with yields of at least 90%. For this purpose use is made with advantage of a reaction medium containing a homogeneous reduction catalyst, such as [Ru(p-cym)$_2$Cl$_2$], a chiral or achiral ligand, in particular a tosylated ligand, such as TsDPEN-(monotosyldiphenylethylenediamine), an organic solvent, triethylamine and a hydrogen source, for example, isopropanol or formic acid.

The derivative E-2 is then obtained with a yield of the order of 90%.

It is also possible to synthesize E-1 or E-2 starting, respectively, from V and from IV, by reduction in an ethanol/water mixture in the presence of NaBH$_4$ and CeCl$_3$.7H$_2$O. The required products are obtained with yields of the order of 95%.

The lactones L-1 and L-4 are obtained on a majority basis, respectively, by reduction starting from E-2 and from E-1. With preference, E-2 is placed in ethanol with RNi under hydrogen, at atmospheric pressure. L-1 is obtained with yields of approximately 75%, the remainder being composed of the other lactones L-2, L-3 and L-4. To obtain L-4 on a majority basis, the method is operated as before but starting from E-1, and the yield is 85%.

In accordance with one preferred embodiment of the invention the isoxazole derivative of formula II is obtained by reacting a hydroxylamine with a 4-keto-2-hydroxy-2-butenoic acid derivative of formula VI:

VI

The hydroxylamine is used more particularly in salt form and the reaction is carried out at ambient temperature.

In the preferred embodiment of the invention the 4-keto-2-hydroxy-2-butenoic acid derivative is obtained by condensing a ketone VII and an oxalate derivative VIII:

VII

VIII

In these formulae, R$_5$ represents an alkyl, such as ethyl or methyl, alkylaryl, vinyl or substituted vinyl radical; R$_4$ and R$_a$ are as defined above. R$_c$ exhibits the significations given by R$_a$ and may be is identical to or different from R$_a$.

In a variant embodiment of the condensation step, the ketone used is 2-butanone. The 4-keto-2-hydroxy-2-butenoic acid derivative leading to 4-hydroxy-isoleucine is then obtained in a mixture with, in particular, a hex-2-enoic acid derivative, these compounds being separated in the course of a subsequent step.

In another preferred variant embodiment of the condensation step, the ketone used is acetone (R$_4$=R$_5$=CH$_3$), leading to the 4-keto-2-hydroxy-2-butenoic acid derivative of formula VI in which R$_3$ is a hydrogen atom and R$_4$ represents CH$_3$. This compound is subsequently functionalized, in particular by alkylation reaction, in the presence of bases and of an alkylating agent.

In yet another preferred variant, the 4-keto-2-hydroxy-2-butenoic acid of formula VI (R$_3$=R$_4$=CH$_3$) is obtained by operating in accordance with the Baylis-Hillmann reaction, by reacting methyl vinyl ketone with a glyoxalate IX, followed either by an isomerization step or by reduction of the double bond and then oxidation of the OH function.

IX

The condensation product formed is isomerized to compound X in the presence of transition metal catalysts.

X

The following intermediates are new products and, accordingly, fall within the scope of the invention: these are products of formulae IV and V in which one of R$_1$ and R$_2$ represents H, the other being other than H; those corresponding to C-1 and C-2, as defined above, irrespective of R$_1$ and R$_2$, and the compounds E-1 and E-2 in which the substituents are as defined above in relation to the compounds IV and V, in which R represents R$_1$ or R$_2$, and the products E-1' and E-2', in which R represents R$_1$ or R$_2$, but differs from H.

The invention is directed most particularly to the preparation of 4-OH-iLeu of formula A by a method comprising the steps of a) synthesis of an ester of pent-2-enoic acid of formula X

X either by reacting 2-butanone with ethyl oxalate or by condensing methyl vinyl ketone with ethyl glyoxalate, followed, without purification, by an isomerization reaction or by a reduction/oxidation sequence;

b) the ester of pent-2-enoic acid obtained reacts with hydroxylamine to form the isoxazole derivative of formula XI,

XI c) the reduction of the isoxazole derivative obtained to give the lactones I-1 to I-4,

I-1

I-2

I-3

I-4 d) the separation of lactone I-1 to I-4 in racemic form, followed by
e) the separation of the enantiomer, leading to the compound A by opening of the lactone, and by
f) the opening of the lactone ring.

Other characteristics and advantages of the invention will be given in the examples which follow, with reference to FIGS. 1 and 2, which represent, respectively, the reaction schemes illustrating the procedural variants for obtaining, from the isoxazole derivative of formula III:
the lactones L-1 to L-4,
the lactones I-1 to I-4.

EXAMPLE 1

Synthesis of pent-2-enoic acid derivatives of formula X

By Functionalization of a Condensation Product of an Anion Derived from Butanone with Diethyl Oxalate A solution of sodium ethoxide is prepared by reacting metallic sodium (6.05 g, 260.00 mmol, 1.2 eq) in anhydrous ethanol (360 mL) at ambient temperature until the metallic sodium is completely consumed. Butanone (20.00 mL, 220.00 mmol, 1.0 eq) is subsequently added dropwise at ambient temperature. After 1 hour of reaction at ambient temperature, diethyl oxalate (60.00 mL, 440.00 mmol, 2.0 eq) is added rapidly dropwise at ambient temperature. After 5 minutes of reaction, the reaction medium is concentrated and then dried under vacuum. The crude reaction product is diluted with saturated aqueous NaCl solution (800 mL) and then the aqueous phase is extracted with ethyl acetate (3×900 mL). The aqueous phase is subsequently diluted in ethyl acetate (900 mL). The aqueous phase is acidified to a pH of 6 with 1N HCl solution, with vigorous magnetic stirring. The organic phase is separated off and the aqueous phase is extracted with ethyl acetate (3×900 mL). The organic phases are combined, dried over $MgSO_4$ and then concentrated under vacuum. The crude reaction product is dried under vacuum to give an isolated yield of 30% of a 90:10 mixture of ethyl 2-hydroxy-3-methyl-4-oxopent-2-enonate and ethyl 2-hydroxy-4-oxohex-2-enoate, and also a product of undetermined structure whose reactivity is identical to that of the product X (m=11.4 g).

The hexanoic acid derivative formed is separated from the compound X by washing with NaCl (sat.), followed by extraction with ethyl acetate. The product X is recovered following acidification of the aqueous phase to a pH of 6 and subsequent extraction with ethyl acetate.

Yield of compound X after washing operations: 30%.

By Functionalization of a Condensation Product of the Anion Derived from Acetone with Diethyl Oxalate Acetone was condensed with diethyl oxalate in a basic medium. The nitrogen groups and the methyl are introduced subsequently.

The compound of formula VI in which $Ra=CH_2CH_3$, $R_3=H$ and $R_4=CH_3$ is functionalized with hydroxylamine hydrochloride to give the compound IV in which $R_a=CH_2CH_3$, $R_1=H$, $R_2=OH$, $R_3=H$ and $R_4=CH_3$, which is subsequently subjected to a methylation reaction to give the same compound but with $R_3=CH_3$.

Ethyl 2-hydroxy-4-oxopent-2-enoate

In a 2-liter three-neck round-bottom flask equipped with a dropping funnel and a paddle stirrer a solution of sodium ethoxide is prepared by reacting metallic sodium (7.74 g, 340.00 mmol, 1.2 eq) in anhydrous ethanol (800 ml) at ambient temperature until the metallic sodium has been completely consumed. A solution of diethyl oxalate (37.20 mL, 280.00 mmol, 1.0 eq) in acetone (10.30 mL, 280.00 mmol, 1.0 eq) is subsequently added dropwise at ambient temperature. The reaction medium is maintained with vigorous stirring for 2 hours. The reaction medium is subsequently concentrated under vacuum. The crude reaction product is diluted in water (200 ml). Ice (100 g) is added, followed by concentrated sulfuric acid (20 ml) in small portions, until a clear orange solution is obtained. The resulting aqueous phase is extracted with ethyl acetate (3×300 mL). The organic phases are combined, dried over $MgSO_4$ and then concentrated under vacuum. The crude reaction product is dried under vacuum to give, quantitatively, the expected product (m=44.71 g).

By Baylis-Hillmann Reaction of Methyl Vinyl Ketone with Ethyl Glyoxalate

The condensation compound is subjected to a step of reduction of the double bond, followed, without purification, by oxidation of the hydroxyl function.

Condensation

A solution of methyl vinyl ketone (5 mL, 50 mmol, 1 eq) in anhydrous dioxane (30 mL) is admixed with a 50% strength solution of ethyl glyoxalate in toluene (14.2 mL, 60 mmol, 1.2 eq), followed by DABCO (600 mg, 0.09 eq). The reaction mixture is stirred at ambient temperature for 24 h. It is subsequently neutralized by adding 10% HCl solution (20 mL) and extracted with ethyl acetate (2×30 mL). The organic phases are combined, dried over $MgSO_4$ and then concentrated under vacuum. The reaction product is recovered with a yield of more than 90%.

Reduction

In a 250-ml single-neck flask, placed under argon, the α,β-unsaturated ketone (8 g, $4.65 \cdot 10^{-2}$ mol) is dissolved in 200 ml of ethanol and then Pd/$CaCO_3$ (1.6 g, 0.2 eq) is introduced into the mixture. The system is purged with hydrogen and stirred permanently under hydrogen pressure at ambient temperature for 3 h 30 min. The reaction medium is filtered over Célite® and the filtrate is concentrated under reduced pressure. The reaction medium thus obtained is employed directly without purification in the oxidation step.

Oxidation

In a 250-ml single-neck flask, which has been flame-treated and placed under argon, a solution of DMSO (2.6 ml, $3.7 \cdot 10^{-2}$ mol) in $CH_2Cl_2$ (120 ml) is cooled to −60° C. and then trifluoroacetic anhydride (6.42 ml, $3.3 \cdot 10^{-2}$ mol) is added. After 10 minutes of stirring at −60° C. the alcohol solution (2. g, $1.15 \cdot 10^{-2}$ mol), diluted in a minimum amount of $CH_2Cl_2$ (12 ml), is added dropwise.

The reaction medium is stirred at −60° C. for 2 h and then triethylamine (7.85 ml, $7.5 \cdot 10^{-2}$ mol) is added dropwise.

The system is stirred at −60° C. for 2 h more and then allowed to return to ambient temperature.

A buffer solution (25 ml) of 0.2M KCl+NaOH, pH=12, is added.

Preparation of the buffer: 25 ml 0.2M KCl, (373 mg+25 ml $H_2O$)+6 ml 0.2M NaOH (2 ml 1M NaOH+8 ml $H_2O$). The aqueous phase is extracted with $CH_2Cl_2$ (2×20 ml) and then the organic phase is dried over $MgSO_4$, reconcentrated under reduced pressure and chromatographed on a silica column (system: 7/3 hexane/ethyl acetate).

The product X (1.5 g) is isolated with a yield of 75%.
Analyses
Compound X

Ethyl 2-hydroxy-3-methyl-4-oxopent-2-enoate

TLC: $R_f$=0.4 (20:80 AcOEt/hexane)
$^1$H NMR ($CDCl_3$, 200 MHz) δ (ppm): 1.36 (s, 6H), 1.97 (s, 3H), 2.23 (s, 3H), 4.23 (m, 4H).
$^{13}$C NMR ($CDCl_3$, 50 MHz) δ (ppm): 11.2; 13.7; 25.4; 61.7; 106.8; 162.9; 168.4; 200.5
IR (v in $cm^{-1}$): 3452 (OH), 3054, 2987, 1731 (C=O), 1264, 742, 703.
MS (CI) m/z: $[M+H]^+$=173.
$T_b$=98° C.; 0.5 mbar.
Colorless Oil Ethyl 2-hydroxy-4-oxohex-2-enoate TLC: $R_f$=0.4 (20:80 AcOEt/hexane)
$^1$H NMR ($CDCl_3$, 200 MHz) δ (ppm): 1.11 (t, $^3$J=7.6 Hz, 3H), 1.31 (t, $^3$J=7.1 Hz, 3H), 2.47 (q, $^3$J=7.6 Hz, 3H), 4.28 (q, $^3$J=7.1 Hz, 3H), 6.31 (s, 1H).
$^{13}$C NMR ($CDCl_3$, 75 MHz) δ (ppm): 8.37; 23.8; 34.1; 62.3; 101.2; 162.0; 165.7; 200.5.
IR (v in $cm^{-1}$): 3452 (OH), 3054, 2987, 1739 (C=O), 1264, 742, 706.
MS (CI) m/z: $[M+H]^+$=173.
Colorless Oil Ethyl 2-hydroxy-4-oxopent-2-enoate TLC: $R_f$=0.5 (50:50 AcOEt/hexane).
$^1$H NMR ($CDCl_3$, 300 MHz) δ (ppm): 1.35 (t, $^3$J=7.2 Hz, 2H), 2.24 (s, 3H); 4.32 (q, t, $^3$J=7.2 Hz, 2H), 6.36 (s, 1H).
$^{13}$C MNR ($CDCl_3$, 50 MHz) δ (ppm): 13.7; 27.2; 62.2; 101.8; 161.7; 166.7; 199.8.
IR (v in $cm^{-1}$): 3561 (OH), 2987, 1739 (C=O), 1643 (C=C), 1602, 1465, 1419, 1370, 1269, 1212, 1119, 1018, 910, 776, 732.
MS (CI) m/z: $[M+NH_4]^+$=176.
Colorless liquid

EXAMPLE 2

Formation of the Isoxazole System XI

Procedure

In a 250-mL two-neck round-bottom flask a solution of 20 mmol of compound X in a 1/1 mixture of anhydrous ethanol/anhydrous tetrahydrofuran (total volume=54 mL) is prepared. The mixture is placed under vigorous stirring and under argon. 1.6 g of hydroxylamine hydrochloride is added in portions (a tenth) over three hours. The mixture is left at ambient temperature for twenty seven hours.

The crude reaction product is diluted in 180 mL of dichloromethane and 110 mL of saturated sodium chloride solution and then the aqueous phase is extracted with dichloromethane (2×110 mL). The organic phases are combined, dried over magnesium sulfate and then, concentrated under vacuum to give an isolated yield of 80% of compound XI.
Analyses
Compound XI
$^1$H NMR ($CDCl_3$, 200 MHz) δ (ppm): 1.36 (t, 3H), 2.07 (s, 3H), 2.33 (s, 3H), 4.37 (q, 2H)
$^{13}$C NMR ($CDCl_3$, 50 MHz) δ (ppm): 7.3, 10.6, 14.1, 61.6, 111.2, 154.7, 160.9, 167.4
MS (CI) m/z: $[M+H]^+$=170
GC/MS $t_R$=8.17 min

EXAMPLE 3

Figure 2:
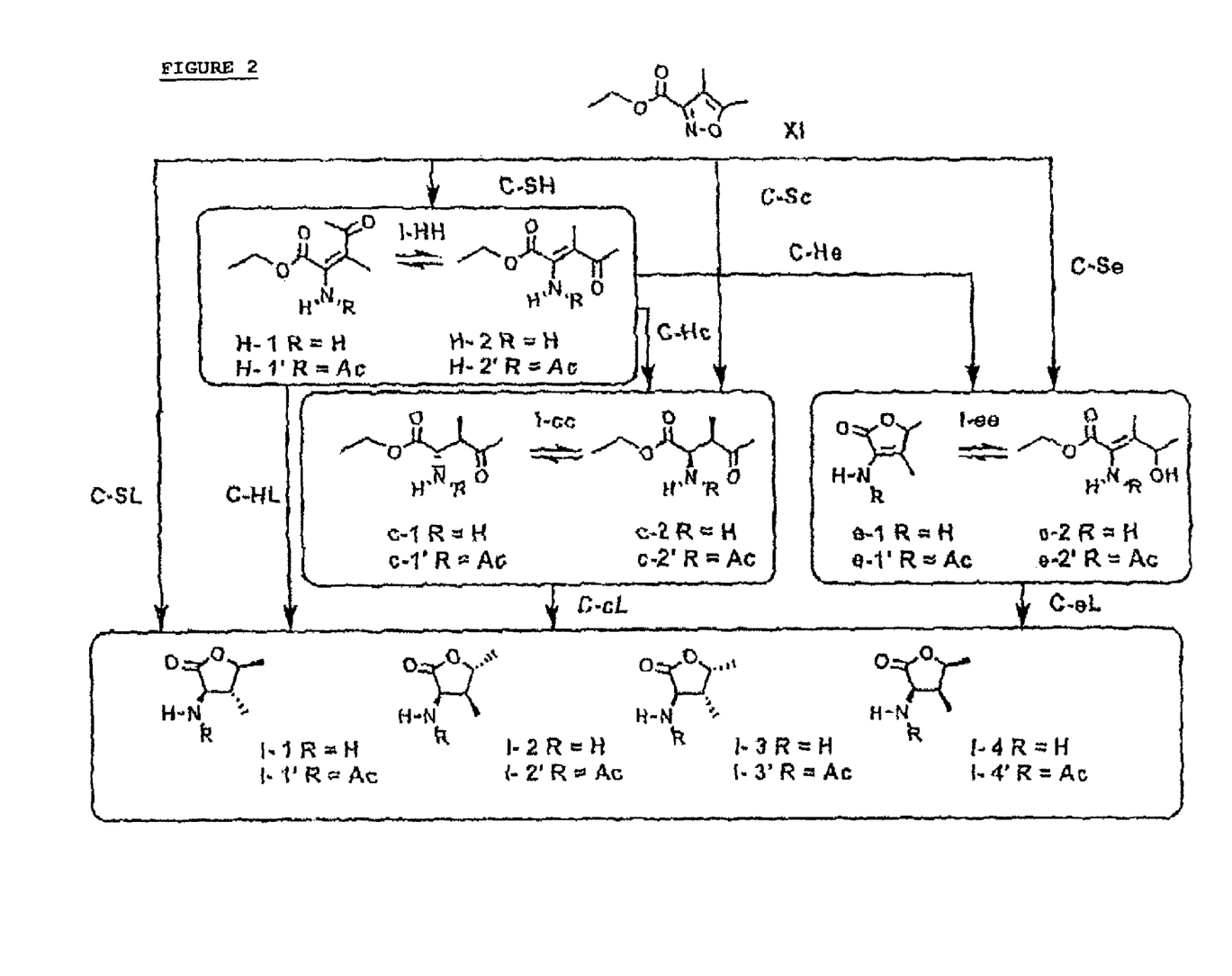
FIG. 2 shows reaction schemes illustrating the procedural variants for obtaining, from the isoxazole derivative of formula III the lactones I-1 to I-4.

Synthesis and Reduction of Intermediates of the Isoxazole System (See Scheme FIG. 2)

Preparation of a solution of Raney nickel in ethanol (solution A)

A commercial solution of Raney nickel in water is centrifuged for 5 minutes at a speed of 4200 revolutions/minute.

The supernatant is removed and the solid is washed with distilled water and then centrifuged again.

This washing cycle is repeated 5 times and then the water is replaced with ethanol to give, after 5 cycles of washing and removal of the supernatant, a volume of Raney nickel of 5 mL (~10 g).

This volume of Raney nickel is then dispersed in 50 mL of ethanol to give a solution A of Raney nickel in ethanol.

Acetylation Procedure

Synthesis of H-1', H-2' from H-1, H-2

In a single-neck round-bottom flask H is placed in acetic anhydride (concentration of 0.45 M) for five hours at 70° C. The acetic anhydride is evaporated under vacuum and the crude reaction product is filtered over silica with an 8/2 hexane/ethyl acetate eluent. The product H' obtained is recrystallized cold from an ether/hexane mixture with a yield of 90%.

Synthesis of l-1', l-2; from l-1, l-2 and c-1', c-2' from c-1, c-2

In a single-neck round-bottom flask, 1 or c is placed in acetic anhydride (concentration of 0.45 M) for one hour at ambient temperature. The acetic anhydride is evaporated under vacuum and the crude reaction product is filtered over silica with an 8/2 hexane/ethyl acetate eluent. The pure product l' or c' is isolated at 98%.

Reaction Conditions C-SL

| Conditions | 1-1 | 1-2 | 1-3 | 1-4 |
|---|---|---|---|---|
| NiR/H$_2$O 50/50 EtOH/H$_2$O AT | 25 | 40 | 10 | 25 |
| NiR/H$_2$O 50/50 EtOH/H$_2$O 55° C. | 40 | 10 | 15 | 35 |
| NiR/DABCO EtOH | 60 | 15 | 10 | 15 |
| NiR/HTMA EtOH | 60 | 16 | 7 | 17 |
| NiR/Et$_3$N EtOH | 33 | 30 | 10 | 27 |

Synthesis of the Lactones l-1 to l-4 with Majority Production of l-2 by Reduction of XI A 5-ml single-neck round-bottom flask is charged with a mixture in equal volumes of ethanol and water (1 mL) the solution A of Raney nickel in ethanol (100 µL) and XI (30 mg, 1 eq, 1.76·10$^{-4}$ mol). The batch is cooled to 0° C. and then purged with hydrogen.

The medium is stirred under hydrogen pressure (1 atm) for 12 hours at ambient temperature.

The crude reaction product is filtered over celite and the mixture of the four lactones is obtained quantitatively.

The lactone l-2 (lactone of 4-hydroxyisoleucine) is isolated by HPLC on a silica column with a yield of 40%.

Synthesis of the Lactones l-1 to l-4 with Majority Production of l-1 by Reduction of XI A 5-ml single-neck round-bottom flask is charged with ethanol (1 mL), DABCO (10 mg), the solution A of Raney nickel in ethanol (100 µL) and XI (30 mg, 1 eq, 1.76·10$^{-4}$ mol). The batch is brought to 0° C. and then purged with hydrogen.

The medium is stirred under hydrogen pressure (1 atm) for 48 hours at ambient temperature.

The crude reaction product is filtered over celite and the mixture of the four lactones is obtained quantitatively.

The lactone l-1 is isolated by HPLC on a silica column with a yield of 60%.

Synthesis of the Lactones l-1 to l-4 with Majority Production of l-4 by Reduction of XI A 5-ml single-neck round-bottom flask is charged with a mixture in equal volumes of ethanol and water (1 mL), the solution A of Raney nickel in ethanol (100 µL) and XI (30 mg, 1 eq, 1.76·10$^{-4}$ mol). The batch is brought to 0° C. and then purged with hydrogen.

The medium is stirred under hydrogen pressure (1 atm) for 12 hours at 55° C.

The crude reaction product is filtered over Célite® and the mixture of the four lactones is obtained quantitatively.

The lactone l-4 is isolated by HPLC on a silica column with a yield of 40%.

The lactones l-1', l-2', l-3' and l-4' are synthesized by acetylating the various crude products obtained above (see acetylation procedure, page 19).

Reaction Conditions C-SH

Synthesis of H-2 by Reduction of COMPOUND XI

A 5-mL single-neck round-bottom flask is charged with ethanol (1 mL), water (50 µL), the solution A of Raney nickel in ethanol (100 µL) and compound XI (30 mg, 1 eq, 1.76·10$^{-4}$ mol). The batch is brought to 0° C. and then purged with hydrogen.

The medium is stirred under hydrogen pressure (1 atm) for 24 hours at ambient temperature.

The crude reaction product is purified by chromatography on a silica column and H-2 is isolated with a yield of 80%.

Reaction Conditions C-SC

Synthesis of c-1 and c-2 by Reduction of COMPOUND XI

| Conditions | c-1 | c-2 |
|---|---|---|
| NiR/DABCO EtOH | 30 | 70 |
| Pd/C/DABCO EtOH | 50 | 50 |
| Pd/C/Et$_3$N EtOH | 70 | 30 |

A 5-mL single-neck round-bottom flask is charged with ethanol (1 mL), triethylamine (50 µL), palladium on carbon (6 mg) and compound XI (30 mg, 1 eq, 1.76·10-4 mol).

The batch is brought to 0° C. and then purged with hydrogen. The medium is stirred under hydrogen pressure (1 atm) for 48 hours at ambient temperature.

The crude reaction product is filtered over celite and the mixture of the two diastereoisomers is obtained in a 70/30 ratio.

The two diastereoisomers c-1 and c-2 are obtained with a yield of 70%.

The compounds c-1' and c-2' are synthesized by acetylating the various crude products obtained above (see acetylation procedure, page 19).

Reaction Conditions C-HL

Synthesis of l-1', l-2', l-3' and l-4' by Reduction of Compound H-2'

A 5-ml single-neck round-bottom flask is charged with a mixture in equal volumes of ethanol and water (300 µL), the solution A of Raney nickel in ethanol (50 µL) and H-2' (10 mg, 1 eq, 0.6 10-4 mol). The batch is brought to 0° C. and then purged with hydrogen.

The medium is stirred under hydrogen pressure (1 atm) for 12 hours at ambient temperature.

The crude reaction product is filtered over Célite® and the mixture of the four lactones is obtained quantitatively.

The lactones l-1', l-2', l-3' and l-4' are isolated by HPLC on a silica column in the following proportions:

| Conditions | 1-1' | 1-2' | 1-3' | 1-4' |
|---|---|---|---|---|
| NiR/H$_2$O 50/50 EtOH/H$_2$O AT | 14 | 13 | 17 | 56 |

Reaction Conditions C-He

Synthesis of e-2' from H-1' or H-2'

In a tube which has been flame-treated beforehand under argon, the reaction medium containing 3 mg of [Ru(p-cym)$_2$Cl$_2$] (5 mol %), the tosylated ligand TsDPEN (1.05 equivalent/Ru), the solvent iPrOH (136 µL) and triethylamine (6.2 µL), is heated at 80° C. for two hours. The medium is then evaporated under argon and left to stand at ambient temperature.

The starting substrate (40 mg) is dissolved in 5/2 HCOOH/NEt$_3$ (92 AL) and the batch is introduced into the tube containing the catalyst for 17 h 00 min at ambient temperature. The crude reaction product is evaporated under vacuum and filtered over silica with ethyl acetate. The product e-2' is isolated with a yield of 90%.

Synthesis of e-1' from H-1' or e-2' from H-2'

The starting substrate is placed in a two-neck round-bottom flask under argon in a 1/1.5 ethanol/water mixture at −15° C. 1.5 equivalents of NaBH$_4$ and 1 equivalent of CeCl$_3$.7H$_2$O are added and the medium is stirred for 15 minutes. The addition of a few drops of acetone allows the excess NaBH$_4$ to be neutralized.

The crude reaction product is diluted in ether and saturated sodium chloride solution and then the aqueous phase is extracted three times with ether. The organic phases are combined, dried over magnesium sulfate and then concentrated under vacuum to give an isolated yield of 95%.

Reaction Conditions C-Hc

Synthesis of c-1 and c-2 from H-2

H-2 is placed under hydrogen at 40 bars in the presence of Pd/C (10% by mass) and ethanol (0.1 M) for 27 h at ambient temperature. The crude reaction product is filtered over celite and evaporated under vacuum. It is obtained with a yield of 55% with a c-1/c-2 ratio of 70/30.

Synthesis of c-1' and c-2' from H-2'

H-2' is placed in ethanol (0.1 M) with 10% by mass of Pd/C under hydrogen at atmospheric pressure for 24 h 00 min. The crude reaction product is filtered over celite and then evaporated under vacuum. A 1/1 mixture of c-1' and c-2' is obtained with a yield of 98%. c-1' and c-2' are separated by HPLC in accordance with the method described above.

Reaction Conditions C-eL

Synthesis of l-1' from e-2' e-2' is placed in ethanol (0.1 M) with commercial Raney nickel under hydrogen at atmospheric pressure. The crude reaction product is filtered over celite and evaporated under vacuum. l-1' is obtained with a yield of 75%. The remaining 25% are a mixture of l-2', l-3' and l-4'.

Synthesis of l-4' from e-1' e-1' is placed under hydrogen in ethanol (0.1 M) at atmospheric pressure in the presence of commercial Raney nickel for 15 h 00 min. The crude reaction product is filtered over Célite® and evaporated under vacuum. l-4' is isolated with a yield of 85%. The remaining 15% represent the acetylated lactone l-2'.

Reaction Conditions C-cL

Synthesis of l-2' from c-1' c-1' is placed in ethanol (0.1 M) in the presence of NaBH$_4$ (2 equivalents) for one hour at 0° C. The crude reaction product is diluted in ethyl acetate and water. The aqueous phase is extracted with ethyl acetate three times. The organic phases are combined, dried over magnesium sulfate and then concentrated under vacuum to give an isolated yield of 75% of acetylated lactone l-2'. The remaining 25% represent the lactone l-4'.

Synthesis of l-4' from c-1'

A 5-mL single-neck round-bottom flask is charged with a mixture in equal volumes of ethanol and water (300 µL), the solution A of Raney nickel in ethanol (50 µL) and c-1' (10 mg, 1 eq, 0.6·10$^{-4}$ mol). The batch is brought to 0° C. and then purged with hydrogen.

The medium is stirred under hydrogen pressure (1 atm) for 12 hours at ambient temperature.

The crude reaction product is filtered over celite and the mixture of the four lactones is obtained quantitatively.

The lactone l-4' is isolated by HPLC on a silica column with a yield of 75%. The remaining 25% represent the lactone l-2'.

Synthesis of l-3' from c-2'

A 5-mL single-neck round-bottom flask is charged with a mixture in equal volumes of ethanol and water (300 μL), the solution A of Raney nickel in ethanol (50 μL) and c-2' (10 mg, 1 eq, $0.6 \cdot 10^{-4}$ mol). The batch is brought to 0° C. and then purged with hydrogen.

The medium is stirred under hydrogen pressure (1 atm) for 12 hours at ambient temperature.

The crude reaction product is filtered over celite and the mixture of the four lactones is obtained quantitatively.

The lactone l-3' is isolated by HPLC on a silica column with a yield of 75%. The remaining 25% represent the lactone l-1'.

Reaction Conditions I-HH

Synthesis H-1' from H-2'

In a tube which has been flame-treated beforehand under argon, the reaction medium containing 3 mg of [Ru(p-cym)$_2$ Cl$_2$] (5 mol %), the tosylated ligand TsDPEN (1.05 equivalent/Ru), the solvent iPrOH (136 μl) and triethylamine (6.2 μl), is heated at 80° C. for two hours. The medium is then evaporated under argon and left to stand at ambient temperature. H-2' is introduced in ethanol (1.1 M) into the catalyst formed and the medium is left for 27 h 00 min at ambient temperature. The crude reaction product is evaporated under vacuum and then filtered over silica with ethyl acetate. H-1' is obtained with a yield of 60%.

Reaction Conditions I-cc

Synthesis of c-1' from c-2' c-2' is placed in ethanol (0.1 M) with 15 equivalents of triethylamine at 80° C for 24 h 00 min. The crude reaction product is evaporated under vacuum and c-1' is isolated with a yield of 55%.

HPLC Conditions

Separation of the Four Lactones l-1', l-2', l-3' and l-4'

The four lactones l-1', l-2', l-3' and l-4' are separated by HPLC.

HPLC (Gynkotek Gina 50) and ZORBAX SIL 4.6 MM ID×25 cm column with a 95/05 hexane/methanol mixture as eluent and a flow rate of 8 mL/min.

Separation of the Two Enantiomers of the Lactone l-2'

The two enantiomers are separated by chiral HPLC. HPLC (Shimadzu) and CHIRALPAK AS column with a 95/5 hexane/ethanol mixture as eluent.

Analyses

The GC/MS analyses are all conducted on the same type of instrument.

GC/MS (Shimadzu GCMS-QP5050A)

Column: SGE CAPILLARY Silica 25 m×0.2 mm PBXS 5 0.25 Carrier gas: helium, flow rate 29 ml/min; pressure: 118 kPa.

Program

Interface: 260° C.

Column: 80° C.

Detector: 320° C.

2 min at 80° C. then temperature increase at 10° C./min

The HPLC analyses are all conducted on the same type of instrument.

HPLC (Gynkotek Gina 50) and ZORBAX SIL 4.6 MM ID×25 cm column

Eluent: 95/05 hexane/ethanol. Flow rate: 8 mL/min

H-1'
$^1$H NMR (CDCl$_3$, 200 MHz) δ (ppm): 1.25 (t, 3H), 1.88 (s, 3H), 2.09 (s, 3H), 2.32 (s, 3H), 4.18 (q, 2H), 7.52 (s, 1H)
MS(CI) m/z: [M+H]$^+$=214
GC/MS $t_R$=12.15 min H-2'
$^1$H NMR (CDCl$_3$, 200 MHz) δ (ppm): 1.33 (t, 3H), 1.91 (s, 3H), 2.10 (s, 3H), 2.26 (s, 3H), 4.37 (q, 2H), 11.85 (s, 1H)
$^{13}$C NMR (CDCl$_3$, 75 MHz) δ (ppm): 13.8, 14.7, 23.5, 29.7, 62, 110.1, 139.1, 164.2, 168.2, 203.8
MS(CI) m/z: [M+H]$^+$=214
GC/MS $t_R$=12.15 min H-2
$^1$H NMR (CDCl$_3$, 200 MHz) δ (ppm): 1.36 (t, 3H), 2.07 (s, 3H), 2.24 (s, 3H), 4.32 (q, 2H), 7.51 (s, 1H)
$^{13}$C NMR (CDCl$_3$, 75 MHz) δ (ppm): 14, 14.9, 29.3, 62, 103.4, 145.3, 165, 202
MS(CI) m/z: [M+H]$^+$=172
GC/MS $t_R$=9.38 min c-1
$^1$H NMR (CDCl$_3$, 300 MHz) δ (ppm): 1.16 (d, 3H), 1.24 (t, 3H), 2.17 (s, 3H), 2.92 (m, 1H), 3.53 (d, 1H), 4.16 (q, 2H)
$^{13}$C NMR (CDCl$_3$, 50 MHz) δ (ppm): 13.3, 14.1, 28.8, 50.3, 56.8, 61, 174.4, 210.2
MS(CI) m/z: [M+H]$^+$=174
GC/MS $t_R$=7.50 min c-2
$^1$H NMR (CDCl$_3$, 300 MHz) δ (ppm): 1.11 (d, 3H), 1.25 (t, 3H), 2.20 (s, 3H), 2.92 (m, 1H), 3.86 (d, 1H), 4.16 (q, 2H)
$^{13}$C NMR (CDCl$_3$, 50 MHz) δ (ppm): 10.8, 14.1, 28.2, 49.6, 55.3, 61.2, 174.2, 209.8
MS(CI) m/z: [M+H]$^+$=174
GC/MS $t_R$=7.60 min c-1'
$^1$H NMR (CDCl$_3$, 300 MHz) δ (ppm): 1.20 (d, 3H), 1.23 (t, 3H), 2.05 (s, 3H), 2.20 (s, 3H), 3.36 (m, 1H), 4.15 (q, 2H), 4.84 (m, 1H), 6.47 (d, 1H)
MS(CI) m/z: [M+H]$^+$=216
GC/MS $t_R$=11.02 min c-2'
$^1$H NMR (CDCl$_3$, 300 MHz) δ (ppm): 1.16 (d, 3H), 1.26 (t, 3H), 1.99 (s, 3H), 2.23 (s, 3H), 3.07 (m, 1H), 4.19 (q, 2H), 4.84 (m, 1H), 6.31 (d, 1H)
MS(CI) m/z: [M+H]$^+$=216
GC/MS $t_R$=11.50 min e-1'
$^1$H NMR (CDCl$_3$, 300 MHz) δ (ppm): 1.47 (d, 3H), 2.10 (s, 3H), 2.15 (s, 3H), 4.92 (q, 1H), 7.31 (s, 1H)
MS(CI) m/z: [M+H]$^+$=170 e-2'
$^1$H NMR (CDCl$_3$, 300 MHz) δ (ppm): 1.23 (d, 3H), 1.29 (t, 3H), 2.03 (s, 3H), 2.08 (s, 3H), 3.64 (s, 1H), 4.22 (q, 2H), 4.58 (m, 1H), 7.61 (s, 1H)
$^{13}$C NMR (CDCl$_3$, 75 MHz) δ (ppm): 13.6, 14.1, 19.5, 23, 61.2, 67.5, 121.6, 146.1, 165.2, 170.2
MS(CI) m/z: [M+H]$^+$=216 e-1
$^1$H NMR (CDCl$_3$, 200 MHz) δ (ppm): 1.4 (d, 3H), 1.84 (s, 3H), 3.39 (s, 3H), 4.79 (q, 1H)
MS(CI) m/z: [M+H]$^+$=128
GC/MS $t_R$=7.59 min l-1'
$^1$H NMR (CDCl$_3$, 200 MHz) δ (ppm): 1.22 (d, 3H), 1.44 (d, 3H), 2.02 (m, 1H), 2.08 (s, 3H), 4.16 (m, 1H), 4.53 (m, 1H)

MS(CI) m/z: [M+H]$^+$=172
HPLC: $t_R$=27 min
l-2'
$^1$H NMR (CDCl$_3$, 200 MHz) δ (ppm): 0.96 (d, 3H), 1.46 (d, 3H), 2.08 (s, 3H), 2.67 (m, 1H), 4.41 (m, 1H), 4.76 (m, 1H)
MS(CI) m/z: [M+H]$^+$=172
HPLC: $t_R$=23.5 min
l-3'
$^1$H NMR (CDCl$_3$, 200 MHz) δ (ppm): 1.16 (d, 3H), 1.32 (d, 3H), 2.07 (s, 3H), 2.55 (m, 1H), 3.07 (m, 1H), 4.19 (q, 2H), 4.84 (m, 1H), 6.31 (d, 1H)
MS(CI) m/z: [M+H]$^+$=172
l-4'
$^1$H NMR (CDCl$_3$, 200 MHz) δ (ppm): 0.80 (d, 3H), 1.38 (d, 3H), 2.09 (s, 3H), 2.94 (m, 1H), 4.56 (m, 1H), 4.70 (m, 2H).
MS(CI) m/z: [M+H]$^+$=172
HPLC: $t_R$=19 min
l-1
MS(CI) m/z: [M+H]$^+$=130
GC/MS: $t_R$=5.7 min
l-2
MS(CI) m/z: [M+H]$^+$=130
GC/MS: $t_R$=6.22 min
l-3
MS(CI) m/z: [M+H]$^+$=130
GC/MS: $t_R$=6.40 min
l-4
MS(CI) m/z: [M+H]$^+$=130
GC/MS: $t_R$=6.69 min Preparation Variant, Starting from the Compound X, of the Compound IV (R$_1$=H, R$_2$=Benzyl, R$_3$=Methyl and R$_4$=Methyl)

The compound X is placed in a two-neck round-bottom flask with activated molecular sieve in anhydrous ethanol. Benzylamine hydrochloride is added in portions (a tenth) over three hours. The mixture is stirred for 24 h at ambient temperature. The crude reaction product is filtered over celite and then diluted in dichloromethane. The organic phase is washed with saturated sodium hydrogen carbonate solution and then with water. The organic phase is dried over magnesium sulfate and then concentrated under vacuum. The crude product is purified by chromatography on silica to give a yield of 50%.

Analyses
$^1$H NMR (CDCl$_3$, 300 MHz) δ (ppm): 1.27 (t, 3H), 1.82 (s, 3H), 2.17 (s, 3H), 4.27 (q, 2H), 4.32 (d, 2H), 7.31 (m, 5H)
$^{13}$C NMR (CDCl$_3$, 50 MHz) δ (ppm): 13.9, 14.9, 28.6, 48.9, 61.7, 97.3, 127.2, 127.5, 128.6, 137.9, 153.0, 164.2, 199.7
MS(CI) m/z: [M+H]$^+$=261

Example of Asymmetric Reduction of the Compound H-2' to Compounds c-1' and c-2'

Preparation of the Catalyst
A Schlenk tube purged beforehand (vacuum, argon) is charged under argon with the catalyst, together with its ligand, in methanol. Stirring is carried out for around 20 minutes until a clear medium is obtained.

Reduction
The substrate is introduced into the autoclave with a bar magnet and, still under argon, the solution prepared above is introduced. The reaction medium is left with stirring for 17 h under hydrogen at 50 bars. The methanol is evaporated and dichloromethane is introduced. Active carbon is added and the mixture is stirred for approximately 15 minutes. The medium is filtered over Célite® and evaporated. The crude product obtained is purified by chromatography on a silica column.

| Catalyst (mol %) Ligand (1.2 eq/cat) | Yield | Proportions c-1'/c-2' | Ratio of enantiomers of c-2' |
|---|---|---|---|
| Rh(cod)$_2$BF$_4$ (4 mol %) + Panephos | 79% | 25/54 | 90/10 |
| Rh(cod)$_2$BF$_4$ (4 mol %) + Binap | 66% | 18/48 | 66/34 |
| Rh(cod)DipampBF$_4$ (4 mol %) | 40% | 0/40 | 96/4 |

The invention claimed is:
1. A method of preparing diastereoisomers and enantiomers of 4-hydroxyisoleucine and derivatives thereof of general formula I in which R$_1$ and R$_2$ represent
a hydrogen atom or
one of R$_1$ or R$_2$ represents a hydrogen atom and the other substituent is a radical R$_a$, an acyl group —COR$_a$, or a functional group —COOR$_a$, SO$_2$R$_a$ or —N(R$_a$,R$_b$), R$_a$ and R$_b$, which are identical or different, being an optionally substituted linear or branched C1-12 alkyl radical, an optionally substituted aryl group containing one or more aromatic rings, comprising 5 to 8 C, or aralkyl, wherein the alkyl substituent of said aralkyl is an optionally substituted linear or branched C1-C12 alkyl radical and the aryl group of said aralkyl is an optionally substituted aryl group containing one or more aromatic rings, comprising 5 to 8 C, or
R$_1$ and R$_2$ are the same,
said method comprising isoxazole derivative of formula II in which
R$_3$ represents a hydrogen atom or R$_a$, and
R$_4$ is an optionally substituted linear or branched C1-C12 alkyl radical, an optionally substituted aryl group containing one or more aromatic rings, comprising 5 to 8 C, or aralkyl, wherein the alkyl substituent of said aralkyl is an optionally substituted linear or branched C1-C12 alkyl radical and the aryl group of said aralkyl is an optionally substituted aryl group containing one or more aromatic rings, comprising 5 to 8 C, to produce the diastereoisomers and enantiomers of 4-hydroxyisoleucine and derivatives thereof of general formula I or to at least one lactone of structure III

III in racemic form(s), or an enantiomerically enriched mixture, followed by the opening, under basic conditions, in a protic or aprotic solvent, of the required lactone or lactones and, optionally, the separation of the required form.

2. The method of claim 1, characterized in that the lactone ring is opened by means of LiOH in THF.

3. The method of claim 1, characterized in that the lactone of structure III is obtained by reducing said isoxazole derivative of formula II, leading to a mixture containing 4 lactones L-1, L-2, L-3 and L-4:

L-1

L-2

L-3

L-4

4. The method of claim 3, characterized in that, where $R_3$ represents a hydrogen atom in the isoxazole of formula II, a group $R_a$ is introduced subsequently into the intermediates obtained.

5. The method of claim 1, characterized in that the desired lactone or lactones is or are separated in racemic or in enantiomerically pure form, the preparation of one of the lactones and/or one of the enantiomers being promoted by the catalyst and the conditions that are used.

6. The method of claim 1, characterized in that the lactones in which $R_1$ and/or $R_2$ represent a hydrogen atom are substituted.

7. The method of claim 1, characterized in that it comprises reducing an isoxazole of formula II in which $OR_a$ represents a hydrogenolysable group.

8. The method of claim 1, characterized in that the intermediates formed during the step of reducing the isoxazole derivative of formula II are isolated.

9. The method of claim 3, characterized in that operation takes place in an ethanol/water medium, to which a solution of Raney nickel in ethanol and the isoxazole derivative of formula II are added, and the mixture is purged with hydrogen, the reaction medium being subsequently stirred under a hydrogen pressure of the order of 1 atmosphere at ambient temperature, giving the derivatives IV and V:

IV

V

10. The method of claim 9, characterized in that the compound V is subjected to the action of a reduction catalyst in a solvent in the presence of a hydrogen source.

11. The method of claim 9, characterized in that the compound IV or V is subjected to the action of a homogeneous reduction catalyst, of a chiral or achiral ligand, in the presence of an organic solvent, of triethylamine and a hydrogen source, or, alternatively, the compounds IV or V are subjected to reduction in an ethanol/water mixture in the presence of $NaBH_4$ and $CeCl_3 \cdot 7H_2O$.

12. The method of claim 1, characterized in that the isoxazole derivative of formula II is obtained by reacting a hydroxylamine with a 4-keto-2-hydroxy-2-butenoic acid derivative of formula VI:

VI

13. The method of claim 12, characterized in that the 4-keto-2-hydroxy-2-butenoic acid derivative is obtained by condensing a ketone VII and an oxalate derivative VIII:

VII

VIII in these formulae, $R_5$ represents an alkyl alkylaryl, vinyl or substituted vinyl radical, $R_c$ exhibits the significations given by $R_a$ and may be is identical to or different from $R_a$.

14. The method of claim 13, characterized in that the ketone used is butanone.

15. The method of claim 13, characterized in that the ketone used is acetone, leading to the 4-keto-2-hydroxy-2-butenoic acid derivative of formula VI in which $R_3$ is a hydrogen atom and $R_4$ represents $CH_3$.

16. The method of claim 13, characterized in that the 4-keto-2-hydroxy-2-butenoic acid of formula VI is obtained by operating in accordance with the Baylis-Hillmann reaction, by reacting methyl vinyl ketone with a glyoxalate of formula IX,

IX followed either by a step of isomerization to compound VI, in the presence of transition metal catalyst, or by reduction of the double bond and then oxidation of the OH function.

VI

17. A method of preparing (2S, 3R, 4S)-4-hydroxyisoleucine, characterized in that it comprises the steps of a) synthesis of an ester of pent-2-enoic acid of formula X

X either by reacting butanone with ethyl oxalate or by condensing methyl vinyl ketone with ethyl glyoxalate, followed, without purification, by an isomerization reaction or by a reduction/oxidation sequence;

b) the ester of pent-2-enoic acid obtained reacts with hydroxylamine to form the isoxazole derivative of formula XI,

XI c) the reduction of the isoxazole derivative obtained to give the lactones I-1 to I-4,

I-1

I-2

I-3

I-4 d) the separation of lactone I-1 to I-4 in racemic form, followed by e) the separation of the enantiomer, f) the opening of the lactone ring, leading to the compound A

18. A compound of formulae IV or V, or C-1, or C-2, or E-1, or E-2, of the following formula:

IV

V

C-1 in which one of $R_1$ and $R_2$ represents H, and the other substituent is a radical $R_a$, an acyl group —$COR_a$, a functional group —$COOR_a$, —$SO_2R_a$ or —$N(R_a,R_b)$, $R_a$ and $R_b$, which are identical or different, being an optionally substituted linear or branched C1-C12 alkyl radical, an optionally substituted aryl group containing one or more aromatic rings, comprising 5 to 8 C, or aralkyl, wherein the alkyl substituent of said aralkyl is an optionally substituted linear or branched C1-C12 alkyl radical and and the aryl group of said aralkyl is an optionally substituted aryl group containing one or more aromatic rings, comprising 5 to 8 C, $R_3$ represents a hydrocien atom or $R_a$, and $R_4$ is an optionally substituted linear or branched C1-C12 alkyl radical, an optionally substituted aryl group containing one or more aromatic rings, comprising 5 to 8 C, or aralkyl, wherein the alkyl substituent of said aralkyl is an optionally substituted linear or branched C1-C12 alkyl radical and the aryl group of said aralkyl is an optionally substituted aryl group containing one or more aromatic rings, comprising 5 to 8 C.

19. The method of claim 1 wherein $R_a$ is acetyl.

20. The method of claim 6 wherein said substituted lactones are alkylated carboxylated, sulfonylated or acylated.

21. The method of claim 6 wherein said substituted lactones are acetylated.

22. The method of claim 13 wherein $R_5$ represents ethyl or methyl.

23. The compound of claim 18 wherein $R_a$ is acetyl.

* * * * *